(12) United States Patent
Akkerman et al.

(10) Patent No.: US 7,821,629 B2
(45) Date of Patent: Oct. 26, 2010

(54) DEVICE AND METHOD FOR DETECTING CONTAMINATION IN A CONTAINER

(75) Inventors: Jensen Peter Akkerman, Huizen (NL); Sjoerd Van Der Zwaan, Bussum (NL); Dan Van Der Meer, Delft (NL); Arend Van De Stadt, Huizen (NL); Frederik Nico Endtz, Rotterdam (NL); Bernardus Cornelis Johannes Landman, Boskoop (NL)

(73) Assignee: Heineken Supply Chain B.V., Zoeterwoude (NL)

( * ) Notice: Subject to any disclaimer, the term of this patent is extended or adjusted under 35 U.S.C. 154(b) by 337 days.

(21) Appl. No.: 10/587,165

(22) PCT Filed: Jan. 27, 2005

(86) PCT No.: PCT/NL2005/000060

§ 371 (c)(1),
(2), (4) Date: Jul. 16, 2007

(87) PCT Pub. No.: WO2005/071391

PCT Pub. Date: Aug. 4, 2005

(65) Prior Publication Data

US 2008/0002182 A1    Jan. 3, 2008

(30) Foreign Application Priority Data

Jan. 27, 2004    (NL) ................................ 1025332

(51) Int. Cl.
*G01N 21/00*    (2006.01)

(52) U.S. Cl. ............... 356/239.4; 356/237.1; 356/242.1

(58) Field of Classification Search ... 356/237.1–241.6, 356/426–431, 600–640
See application file for complete search history.

(56) References Cited

U.S. PATENT DOCUMENTS 3,651,937 A * 3/1972 Kronseder ............... 209/524
4,136,930 A * 1/1979 Gomm et al. ............ 348/127
4,160,601 A * 7/1979 Frosch et al. ............ 356/404
4,280,624 A * 7/1981 Ford ....................... 209/524
4,650,326 A * 3/1987 Nagamine et al. ........ 356/239.4

(Continued)

FOREIGN PATENT DOCUMENTS

| CN | 1238451 A | 12/1999 |
|---|---|---|
| EP | 0872724 | 10/1998 |
| EP | 872724 A2 * | 10/1998 |
| EP | 0957355(A2) | 11/1999 |
| EP | 0999047 | 5/2000 |

(Continued)

OTHER PUBLICATIONS

Chinese Office Action dated Jan. 8, 2010 in CN Application No. 200580003266.0.

*Primary Examiner*—Gregory J Toatley, Jr.
*Assistant Examiner*—Jarreas C Underwood
(74) *Attorney, Agent, or Firm*—Harness, Dickey & Pierce, P.L.C.

(57) ABSTRACT

A device is disclosed for determining the possible presence of contamination of a container with a decorative exterior, for instance provided with a labelling and/or relief patterns, for liquids such as a drink such as beer or a soft drink. The device includes an irradiating device for irradiating the container with at least a first wavelength (for instance visible light, infrared, ultraviolet, x-radiation), and a recording device for recording a radiation sample of radiation after it has had interaction with at least a part of the container. Further, an orientation determining device is included for determining the orientation of the container relative to the recording device, along with a comparing device for comparing the sample to a reference matching the orientation of the container relative to the recording device during the recording to determine the possible presence of contamination.

23 Claims, 5 Drawing Sheets

U.S. PATENT DOCUMENTS

| | | | |
|---|---|---|---|
| 4,676,650 A * | 6/1987 | Bjorndal et al. | 356/427 |
| 4,691,231 A | 9/1987 | Fitzmorris et al. | |
| 4,945,228 A * | 7/1990 | Juvinall et al. | 250/223 B |
| 5,067,616 A * | 11/1991 | Plester et al. | 209/3.1 |
| 5,374,988 A | 12/1994 | Wertz et al. | |
| 5,405,014 A * | 4/1995 | Krieg et al. | 209/524 |
| 5,444,535 A * | 8/1995 | Axelrod | 356/369 |
| 5,969,810 A | 10/1999 | Nicks et al. | |
| 5,987,159 A | 11/1999 | Nichani | |
| 6,067,155 A | 5/2000 | Ringlien | |
| 6,448,549 B1 * | 9/2002 | Safaee-Rad | 250/223 B |
| 6,660,469 B1 * | 12/2003 | Wright et al. | 435/4 |

FOREIGN PATENT DOCUMENTS

| | | |
|---|---|---|
| EP | 1241467 | 9/2002 |
| WO | 97/04887 | 2/1997 |
| WO | 03/042673 | 5/2003 |

\* cited by examiner

DEVICE AND METHOD FOR DETECTING CONTAMINATION IN A CONTAINER

The present invention relates to systems for selecting containers, for instance provided with labelling and/or relief patterns, for liquids such as a drink such as beer or a soft drink, for the possible presence of contamination of the container.

Systems for detecting contamination present on the inside of a container are known, for instance for bottles used in a rotating system wherein these bottles are supplied to consumers a plurality of times, wherein they are taken back by a supplier after a use in order to be refilled with the required product. An inspection for interior contamination can also be provided for bottles for once-only use.

Such known systems function by illuminating the container from one side and then making an image recording of the illuminated bottle. Contaminants can hereby be viewed on the image recording.

However, when containers are used with a decorative exterior, for instance provided with a labelling and/or relief patterns, such a system is inadequate. The decorative exterior for instance prevents viewing of the contamination and/or is itself viewed as contamination on the recording.

In order to prevent such drawbacks, the present invention provides a device for detecting the possible presence of contamination of a container with a decorative exterior, for instance provided with a labelling and/or relief patterns, for liquids such as a drink such as beer or a soft drink, comprising:

- irradiating means for irradiating the container with at least a first wavelength,
- recording means for recording a radiation sample of radiation during interaction of the radiation with at least a part of the container,
- orientation determining means for determining the orientation of the container relative to the first recording means,
- comparing means for comparing the sample to a predetermined reference matching the orientation of the container relative to the first recording means during the recording.

An embodiment according to the present invention has the advantage that it can take into account the decorative exterior when determining whether contamination of the container is present. If a recording is made of for instance a bottle of which the orientation is known, this can be used to determine whether there is a difference between the current bottle and this reference by means of a reference associated with this orientation, i.e. a previously recorded image or a processing of previously recorded images. If this is the case, this difference indicates the presence of contamination. Such a bottle must be rejected. It is therefore possible to perform an inspection for the possible presence of contamination, even if the container comprises a decorative exterior. Ornaments extending round the whole of the periphery of the container can here also be taken into account.

In a preferred embodiment the device comprises second recording means for recording radiation (1) at a different moment, and/or position (2), and/or (3) with another wavelength which is generated by a second irradiating means. This radiation sample can be used to determine the orientation of the container relative to the first recording means. In a further embodiment, the device comprises for this purpose means for determining the orientation of the container relative to the first recording means on the basis of the relative positions of the first recording means, the second recording means and the container at the time of the first and second recording. It is not necessary here for both the recordings to be made at the same moment or for the container to be situated at the same position, or even orientation, during the respective recordings. During the inspection the container is advanced by means of a conveyor and can optionally undergo an orientation rotation that is known in advance (for instance by a known bottle rotation in a so-called carrousel machine).

Recording data from the second recording means are preferably used to determine the orientation of the container relative to the first recording means. These recordings can further be used to evaluate the quality of the decorative exterior. Use is herein made of an assessment system as described in international patent application WO 03/042 673 A1 of the same applicant. The text of this application should be deemed as included herein, wherein the method for generating a robust reference image of a container and the method for assessing a container by means of the robust reference image are of specific importance. In preferred embodiments to be described hereinbelow, the reference for the comparing means is formed by means of a method for producing a robust reference image of a container as according to this earlier application. Using the images from the second recording means it is also possible, in addition to determining the orientation of the container relative to the first recording means, to assess the decorative exterior of the container on the basis of the method of the above stated application.

In a further preferred embodiment, the device comprises filter means for making recordings in optically independent manner with the recording means on the basis of radiation of the first or of the second wavelength. These filter means provide the advantage that the recordings of the first recording means and those of the second recording means can be made simultaneously of a container for both the above described objectives, i.e. detecting the possible presence of contamination of a container and assessing the quality of the decorative exterior of the container. These filter means for instance comprise an optical filter or an electronic filter.

An optical filter can be embodied so that it is partly selectively permeable to radiation of a determined wavelength range. The filter can herein be placed at an angle relative to the radiation to be transmitted or filtered. Such a filter makes it possible to make recordings simultaneously by means of the first and second recording means. Alternatively, it is also possible to make the recordings one after the other.

The filter means can alternatively comprise an electronic filter wherein the radiation-sensitive elements of the recording means are for instance only sensitive to determined wavelengths, or in which wavelengths of different magnitudes are highlighted from the data after making of the recording by the recording means.

The first radiation sources are positioned relative to the first recording means preferably on the rear side of the position of the container during making of the recordings, wherein the radiation irradiates the container. It hereby becomes possible to inspect the front and rear wall of the container simultaneously. The device preferably comprises selecting means for selecting a part of the recording of a part of the container as assessment part, on the basis of which part the assessment is carried out. It hereby becomes possible to highlight the most important parts of the container which must be selected from the whole recording. Such a partial recording can for instance be used to exclude from the inspection non-relevant disturbances relating to the content of the container. It may occur for instance that temporary foaming occurs at the position of the underside of a printed label, which could result in a container being rejected. In such a case the selection can be made smaller so that the underside of the label is not assessed.

In the case of a round container such as a bottle, the distortion close to the sides of the recording is also relatively great. It is therefore advantageous not to use in the assessment a part of the recording having such a distortion.

The recording means comprise at least one camera. Such a camera may for instance be sensitive to infrared, normal or ultraviolet light; other radiation is however possible. Use can also be made of polarized light to enable optimal detection of determined contaminants. In the descriptions following hereinbelow, any reference to light is also understood to include the option of using polarized light. The use and filtering of polarized light are per se known, the present invention provides the use hereof in a detection method. The choice of such a camera and the radiation source preferably depends on parameters of the containers. If the container is for instance a green bottle with a printing, a different radiation source and camera combination will optionally be chosen than when the container meets other specifications.

In a further embodiment the device further comprises composing means for composing, on the basis of the first and/or second radiation sample and/or predetermined parameters, a robust reference image or a reference image with permissible deviation values, on the basis of which image acceptable deviations in the decorative exterior within a series of containers can be taken into account during selection of containers. This provides the advantage that statistically anticipated deviations in containers of the same type relative to the prescribed specification of the containers of the same type can be taken into account.

The device further preferably comprises processing means for producing, on the basis of the radiation sample or the assessment part, a flat representation thereof. The operation of such processing means is likewise described in the above mentioned international patent application WO 03/042 673. Such a flat representation has the advantage that the whole reference image is constructed in compact manner by connecting flat part-reference images.

The first comparing means are preferably embodied in order to compare the flat representation to the robust reference image. The advantages of the above described preferred embodiments are hereby combined.

In order to enable the comparison of the decorative exterior by means of the second recording means, the device preferably comprises second comparing means for comparing a recording of the second recording means to a second reference image or robust reference image for the purpose of detecting deviations of the decorative exterior. Using these second comparing means, a method for assessing the decorative exterior can be performed by the present invention.

The orientation determining means preferably determine the orientation on the basis of the recording of the second recording means. By means of recordings by the first and second recording means the device can hereby have available all information required to determine whether possible contamination is present on the inside as well as to determine whether the decorative exterior meets the specifications.

According to a further aspect of the present invention, there is provided a device for detecting the possible presence of contamination of a container with a decorative exterior, for instance provided with a labelling and/or relief patterns, for liquids such as a drink such as beer, comprising:
  irradiating means for irradiating the container substantially from the top or the bottom with at least a first wavelength,
  recording means for recording a radiation sample of radiation after it has passed through at least one wall part of the container,
  comparing means for comparing the sample to a predetermined reference of the container relative to the first recording means during the recording.

An advantage of an embodiment according to this aspect is that a recorded radiation sample only comprises image information relating to the side of the container directed toward the recording means. The comparison can thus be made by the comparing means without information relating to the orientation of the container.

The device according to claim 18 preferably comprises one or more measures as specified in the foregoing.

A further aspect of the present invention relates to a method for detecting the possible presence of contamination of a container with a decorative exterior, for instance provided with labelling and/or relief patterns, for liquids such as a drink such as beer, comprising steps for:
  irradiating the container with radiation with at least a first wavelength by means of irradiating means,
  determining the orientation of the container relative to the first recording means,
  recording by means of recording means a radiation sample of the radiation after the radiation has passed through at least a part of the container,
  determining the possible presence of contamination by comparing the sample to a predetermined reference matching the orientation of the container relative to the recording means,
  approving or rejecting the container.

Preferred embodiments comprise steps for determining the orientation of the container making use of radiation comprising at least a second wavelength, and making recordings by means of second recording means with a sensitivity to the second wavelength.

Advantages of embodiments of this aspect of the invention are similar to those specified in the foregoing.

Further advantages, features and details of the invention will be described on the basis of embodiments with reference to the accompanying figures, in which.

Figure 1:
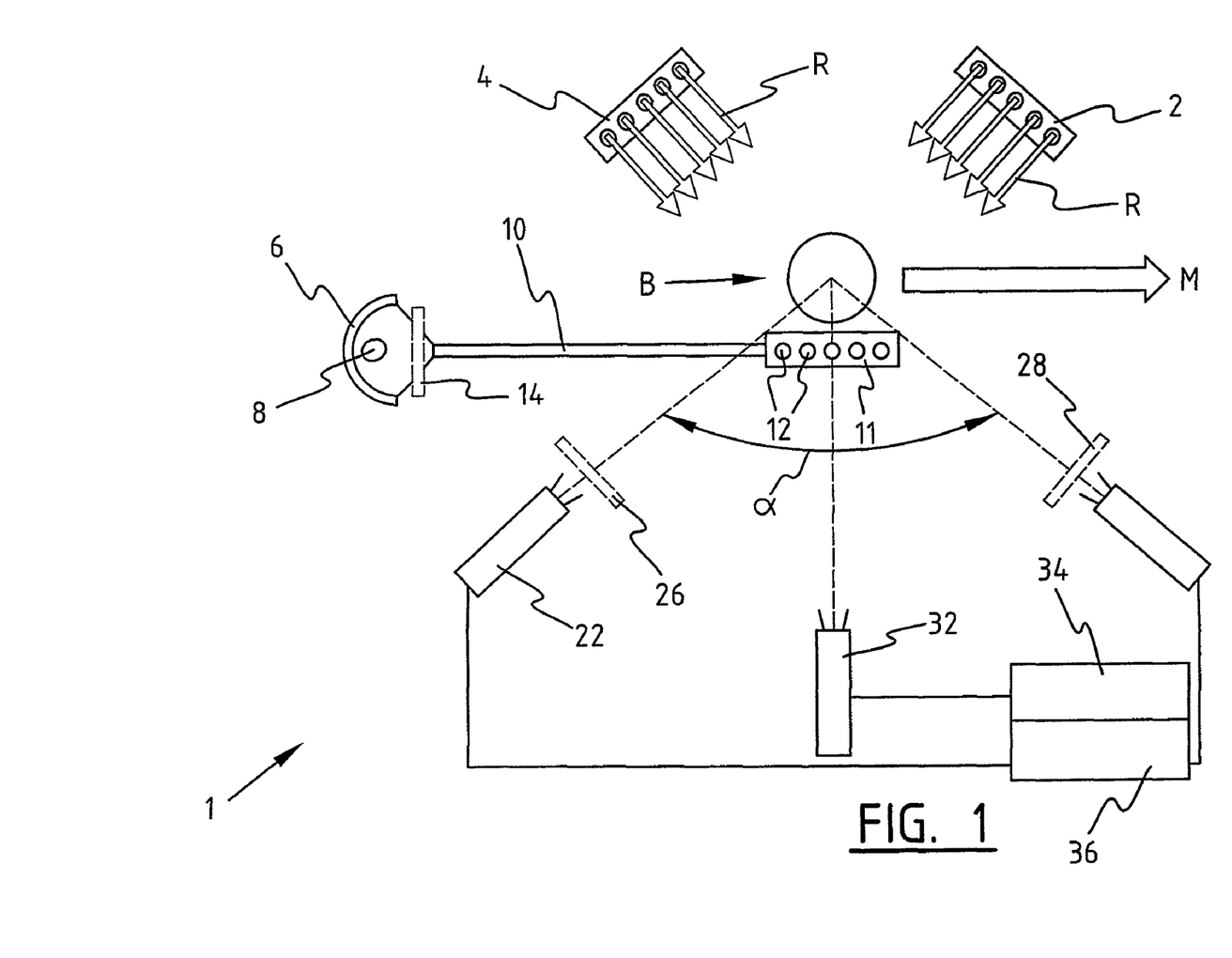
FIG. 1 shows a schematic representation of a system according to a preferred embodiment according to the present invention.

FIG. 1 shows a schematic top view of a first embodiment according to the present invention. One bottle B is shown, although in practice a series of bottles is transported through the detection device in the direction of arrow M by means of a conveyor (not shown). At the location of the shown bottle B diverse recordings are made of the bottle in order to carry out the desired detection.

Two cameras 22, 24 are situated at an angle of for instance 90°, which cameras are in this preferred embodiment sensitive to infrared radiation or light in the infrared range. Depending on the type of bottle or other container, and the decorative exterior thereof, other recording means or cameras with a sensitivity to other wavelengths can be applied.

Opposite each camera 22, 24 are situated infrared light emitters 2, 4 which can emit infrared radiation R in the direction of the cameras. The infrared light radiated through bottle B is then picked up by means of cameras 22, 24.

The system further comprises processing means 36, comprising for instance a computer for processing the recording data from cameras 22, 24. Processing means 36 can also comprise two computers, one for each camera.

In the detection of contamination in accordance with the setup described up to this point, processing means 36 receive, per image recording, images which comprise the possible contamination as well as data relating to the decorative exterior, such as labelling that is present and/or relief patterns in the glass of the bottle. If every presence of radiation-blocking elements in the wall of the bottle were to result in rejection of a bottle, information relating to the labelling and/or the relief patterns would be assessed as contamination and therefore result in rejection of the bottle. This is undesirable. Information relating to the relief patterns and the labelling is therefore stored in the memory means of computer 36. Using this stored information, account can be taken of this information by means of a suitable processing, so that the labelling and/or the relief patterns will not result in rejection.

This information is present in the form of reference images. In order to take into account acceptable, for instance slight deviations in the decoration, the acceptable deviations within a type of bottle are included in a so-called robust reference image by means of statistical processes in a manner known from WO 03/042673. These robust reference images are stored per type of bottle, whereby a plurality of types of bottle can be processed with the same method using one device. For the sake of completeness, this processing is further explained hereinbelow.

A further improvement in the efficiency with which one or more processing unit(s) 36 performs the inspection is by storing a plurality of robust reference images. 120, 360 or 720 robust reference images of a bottle are for instance stored here, with a relative rotation of respectively 3, 1 or half a degree. By means of a suitable processing the computer can hereby use the most closely matching reference image for the present recording of bottle B.

In order to efficiently select the correct robust reference image with the correct orientation during the recording, the orientation of the bottle relative to camera 22, 24 is preferably known. Camera 32 is situated for this purpose in the device. Camera 32 serves to make an elevation recording of the exterior of the bottle, on the basis of which recording processing unit 34, which either comprises a program which functions on the same computer as processing unit 36 or can be provided in a separate computer, serves during the recording to determine the orientation of the bottle on the basis of this recording. Using the orientation of bottle B determined by means of the recording of camera 32, processing unit 36 can determine the robust reference image with the correct orientation. For an optimal result of the recording of camera 32, an illumination of bottle B is further provided from the front side relative to camera 32. Arranged for this purpose adjacently of the conveyor of the bottles is a bracket 11 in which are situated the ends 12 of light-conducting fibres such as glass fibres 10. By means of these glass fibres 10 light from a light source 8, which is centralized by means of a reflector 6 and which is filtered by means of a filter 14, is supplied to the bracket.

The wavelength of lamp 8 is preferably different from that of radiation sources 2 and 4. Cameras 22 and 24 on the one hand and camera 32 on the other hereby function without influencing each other.

Filters 14, 26 and 28 are provided in order to further reduce this mutual influencing. When the wavelength as specified in the foregoing is used in this embodiment, filter 14 serves to filter out infrared light generated as side-effect by source 8. Filters 26, 28 further serve to filter out the for instance visible light of light source 8. An alternative method of filtering is by means of a semi-specular filter 26, disposed at 45°, which reflects the visible light sideways and is permeable to the infrared light. In this version the filter placed at 45° to the infrared beam can reflect the visible light in the direction of a camera 32 which is directed at the obliquely placed filter. This version is not shown.

Figure 2:
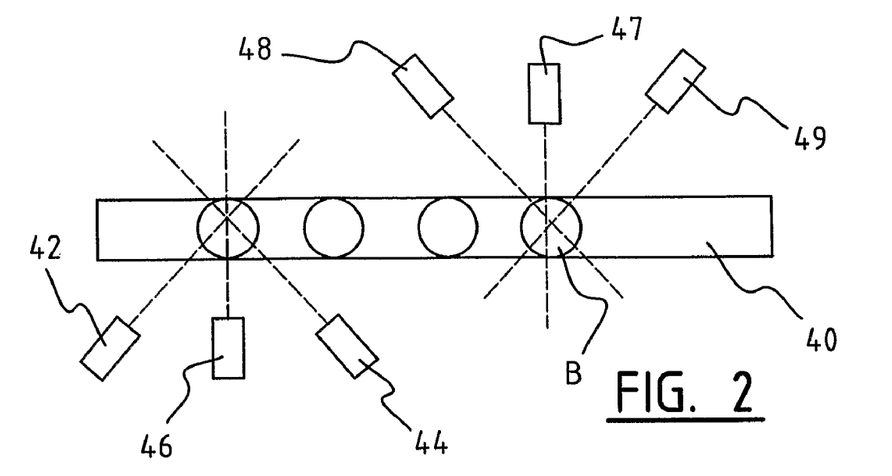
FIG. 2 shows a schematic representation of a part of a further preferred embodiment.
Figure 3:
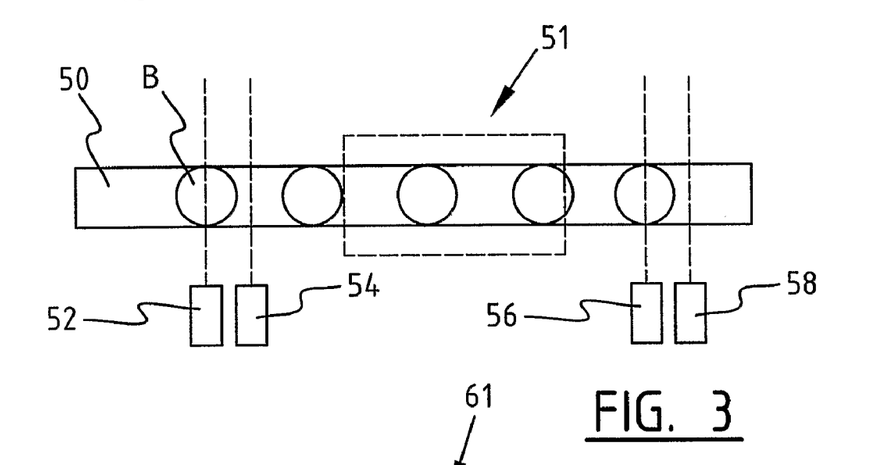
FIG. 3 shows a schematic representation according to a further preferred embodiment.
Figure 4:
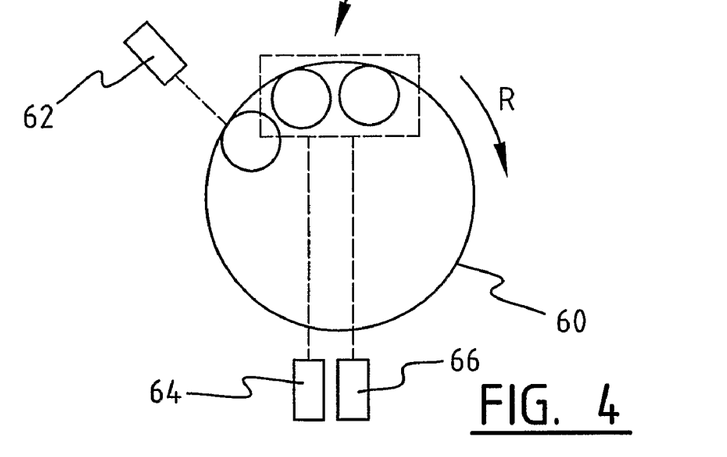
FIG. 4 is a schematic representation of a further preferred embodiment.

FIGS. 2, 3 and 4 show schematically alternative embodiments of the camera layout. FIG. 2 herein shows a doubling of the camera arrangement of FIG. 1. Cameras 42 and 44 correspond here to the cameras of the first type 22 and 24 of FIG. 1, and camera 46 corresponds to the camera of the second type 32 of FIG. 1. Since this camera layout inspects a part of the bottle, in this embodiment a second camera layout is arranged on the other side of the conveyor. Cameras 48 and 49 of the first type are herein used for the same function as cameras 42 and 44, and camera 47 of the second type is used for the same function as camera 46. Illuminating means as according to the embodiment of FIG. 1 are likewise present in this embodiment in a manner which is not shown.

FIG. 3 shows a conveyor 50 with a series of bottles B thereon. Module 51 serves to rotate the bottle through a predetermined number of degrees between measurements by the first camera group, comprising cameras 52 and 54, and the second camera group, comprising cameras 56 and 68. This angle is for instance 90°. Cameras 52 and optionally 56 are of the first type for making a recording of the decorative exterior of the bottle, and cameras 54 and 58, and optionally 56, are of the second type for making the recording (with for instance infrared light, as specified in the foregoing) for the contamination inspection on the interior. The recordings of camera 52 and optionally 56 serve to determine the position of the bottle relative to the camera of the first type.

A further embodiment (FIG. 4) shows a measuring arrangement in a carrousel. The carrousel herein rotates in the direction of the arrow R. Two cameras 64, 66 of the first type make recordings, and a camera 62 of the second type for determining the orientation of the bottle also makes recordings. The illuminating means are not shown in this schematic representation. A rotation unit 61 can optionally be incorporated in the carrousel for the purpose of rotating the bottle to a second orientation in order to obtain more measurement data of a bottle.

Other embodiments are also possible, wherein at least one camera of type one and at least one camera of type two are used, and the bottle rotates a known number of degrees between the two camera recordings. The use of a plurality of cameras per type will increase the detection reliability. The detection reliability will also be increased by focussing the camera on the front side of the bottle and applying an extra camera for the rear of the bottle.

In the above described embodiments the position of the lighting and the camera relative to the bottle can be varied by means of placing mirrors between the lighting, the bottle and the camera in appropriate manner. It hereby becomes possible for instance to place all cameras parallel to the conveyor, whereby the device can be given a relatively compact form.

Figure 5:
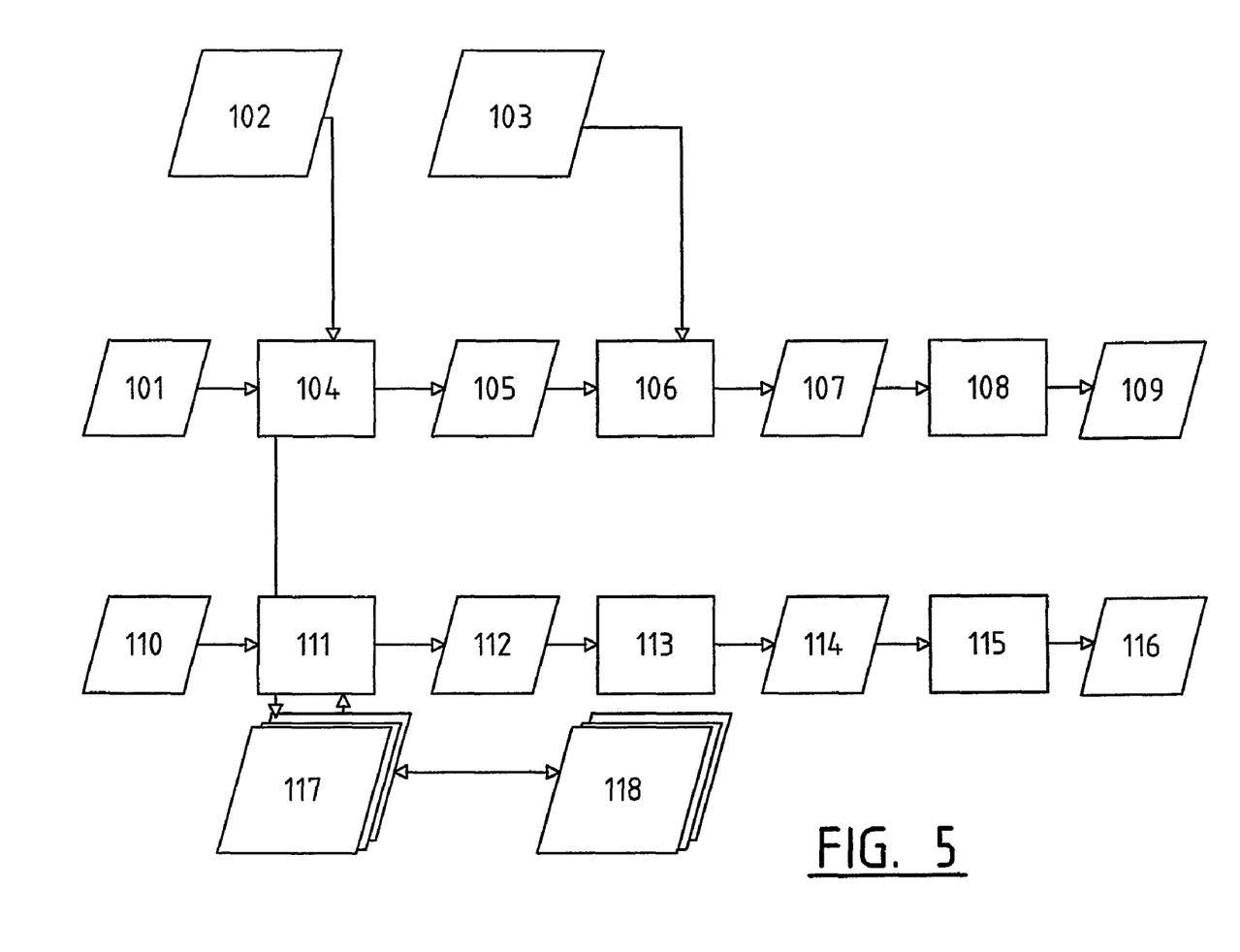
FIG. 5 shows a flow diagram of a method according to an embodiment according to the present invention.

The operation of processing units 34 and 36 is now set forth with reference to FIG. 5. The steps 101, 104-109 are performed by processing unit 34 of the embodiment of FIG. 1. Steps 110-116 are performed by processing unit 36 of the computer of FIG. 1. The recorded image 110 is fed to the processing unit. Step 111 makes use of information originating from step 104, the recorded image from a camera of the first type 110 and a reference image 117 stored in a memory of the computer.

A number of reference images is stored per type of bottle. These are for instance 360 images, or one image per degree of rotation, or 720 images, or two images per degree of rotation. Using such a quantity of images a suitable reference image can be chosen at each orientation of the bottle relative to the camera of the first type. In step 111 the correct reference image is selected on the basis of the orientation data obtained from step 104, which reference image is then used as compensation for recorded image 110, the orientation of which is obtained from step 104.

From this step 111 there results a differential image 112. This differential image 112 undergoes a further processing in step 113. In order to prevent unnecessary rejection of bottles on the basis of production variations during arranging of the labels or the relief patterns, a robust reference image in which acceptable differences are processed in statistical manner is taken into account in this step. The acceptable differences which can be detected in differential image 112 as a result of product variations are eliminated by means of step 113 by compensating the so-called robust differential image with (for instance by subtracting it from) differential image 112. The result of this processing is filtered differential image 114. 360 or 720 variants of the robust differential image 118 are for instance also stored. This is advantageous for both images 117, 118, since using these stored images relatively little computing power is required to select the correctly oriented image for performing this method. An alternative herefor is that a suitable reference image is first selected on the basis of an overall recording of the bottle, by means of processes requiring a relatively large amount of computing power.

Figure 7:
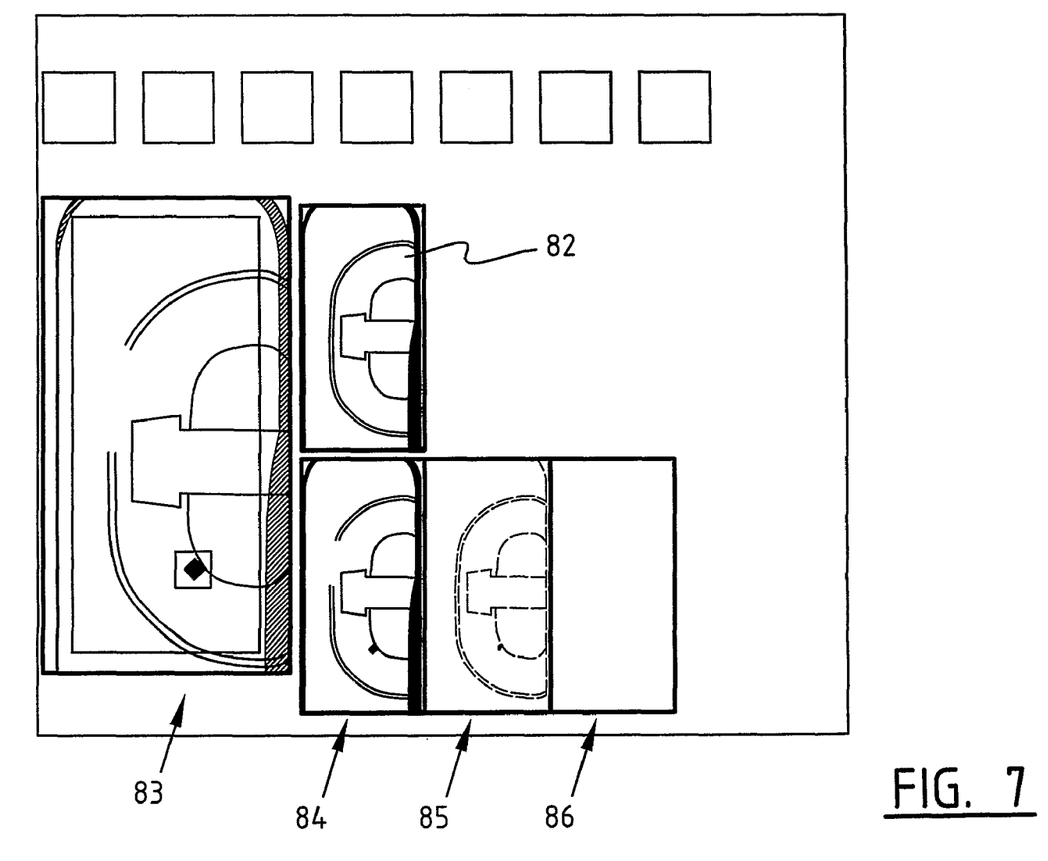
FIG. 7 is a schematic representation of a computer screen according to the present invention.

The filtered differential image of 114 is then analysed in step 115. This filtered differential image is shown in FIG. 7 by means of reference numeral 86. It can be seen clearly here that a dark dot is present, which will have to result in rejection. The result of this analysis is an indicator 116 which can either have the value of approved or rejected.

FIG. 7 shows an example of a graphic representation of a software program suitable for performing the method for detecting the possible presence of contamination of the bottle with the decorative exterior. Operation takes place here on the basis of a translucent image wherein the light radiates through the bottle for a recording. Several software control buttons of the software are shown at the top. On the left is shown the recording 83 of the bottle which corresponds with received image 110, having therein in a rectangle the area for assessing, comprising for instance 60 degrees of the periphery of the bottle. In this representation a solid with a square around it is shown at the bottom of the label. This solid represents a contamination of the bottle behind the label.

Adjacently above this latter the reference image which is a recording of an irradiated standard bottle of this type is indicated by numeral 82. This corresponds to reference image 117 from the method description. Below this the received translucent image 84 (in the same way as image 110) is shown once again reduced in size. The contamination can also be viewed hereon at the same position as in representation 83. Adjacently thereof the differential image 85 corresponding to differential image 112 is shown. This differential image is the difference between the representation of 84 and that of 82. The contamination is also visible hereon.

In the representation of differential image 85 the broken lines show that an individual bottle is subject to production deviations in respect of the decorative exterior. The alignment of a label can vary somewhat, as well as the positioning thereof. In order not to allow an imperfectly positioned or dimensioned label to result in rejection as if it were contamination, this differential image 85 is compensated with the robust differential image or mean differential image 118. The result of this process is representation 86, in which all residues of the decorative exterior, being the labels and relief patterns, are eliminated. The contamination remains visible after these treatments. A bottle is rejected on the basis of the detected contamination.

Set forth in the foregoing is the method for inspecting a bottle with a label and relief patterns arranged thereon. In a preferred embodiment use is herein made of the orientation of the bottle relative to the camera of the first type during the recording. This recording for determining the orientation is preferably combined with a recording for inspecting the quality of the decorative exterior, or the label and the relief patterns.

For this purpose a recorded image 101 is made by means of camera 32. In step 104 a part of this recorded image which is important is processed into a flat representation of the exterior of the bottle. This representation corresponds to an exterior of the bottle placed in a flat plane. On the basis of label reference image 102 it is then determined which part of this reference image corresponds with recorded image 101. The orientation of the bottle relative to the camera is then calculated on the basis of this operation. Data relating to this orientation from step 104 are fed to step 111. In step 104 the label reference image 102 is then processed with the recorded image 101. This results in the label differential image 105.

In order to be able to take into account natural or acceptable differences between manufactured bottles in respect of the printing on the exterior, the mean label differential image 103 is composed. This mean or robust label differential image 103 comprises known or measured data relating to acceptable deviations relative to the specifications of the bottle. In step 106 the label differential image 105 is compared to the mean label differential image 103 by means of a calculating operation. This results in the filtered differential image 107. In step 108 an assessment is made as to what extent the resulting filtered differential image 107 comprises information relating to unacceptable differences. On the basis of this analysis the bottle is approved or rejected in step 109.

The mean label differential image 103 and the mean differential image 118 for the side wall inspection are produced during a learning procedure with a series of "good" bottles. A sufficiently large series of "good" bottles contains a number of bottles which fall just within the tolerance in respect of the quality of the label and/or the relief patterns. The quality margin of the mean differential images is determined on the basis hereof. For every 1 degree of rotation for instance a mean differential image 118 is produced on the basis of translucent radiation. During recording of images for producing the mean differential image 118 it is important that the orientation is known in order to determine each of the for instance 360 mean differential images 118. It is however recommended that the orientation of the bottle is known during normal operation. It is however also possible to perform the method 110-118 without the orientation being known. In step 111 a greater amount of computing power is here required to determine the orientation in order to enable comparison of the received image 110 with the reference image in the correct orientation.

Figure 6:
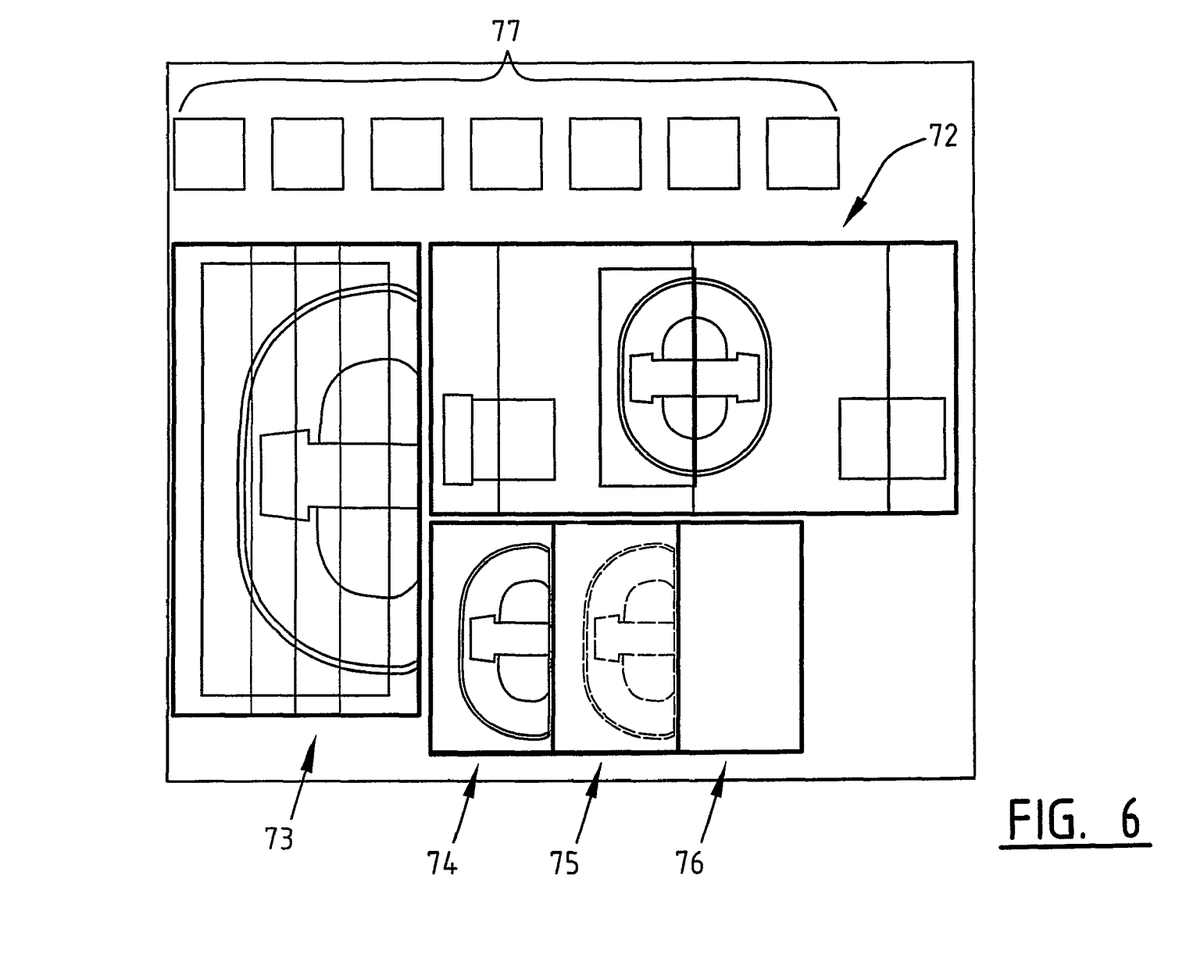
FIG. 6 shows a schematic representation of a computer screen of an embodiment according to the present invention.

FIG. 6 relates to a screen representation of a software program used to determine the orientation of the bottle relative to the camera, and optionally to determine the quality of the decorative exteriors. Here 73 relates to a representation of an elevation recording of the bottle having therein a rectangle which relates to the part of the bottle to be assessed. The deviation herein also becomes relatively great close to the edges of the recording. Representation 72 relates to an exterior of the bottle which has as it were been laid in a flat plane. Representation 73 relates to the recording 102. Representation 74 relates to the "unrolled" image which is made in step 104 of the received image 101 for comparison to the label reference image 102. The orientation of the bottle can be determined on the basis of this comparison.

In order to determine the quality of the label on the exterior, the label differential image 105 is produced, this being shown in representation 75. All possible colour of the label is hereby also used and processed in order to arrive at a representation in grey tones representative of deviations. Finally, the filtered differential image 107 is shown by means of 76. In this case it is a label without deviations. In the case of deviations, spots of a determined pixel size are shown in representation 76. If the spots include a sufficient number of pixels, a decision is made to reject the label. (A combination of) other criteria, such as shape or location of the deviation, can also result in rejection.

Different aspects of the above described embodiments can be mutually varied in order to arrive at non-described specific embodiments. The rights sought are defined by the appended claims.

The invention claimed is:

1. Device for determining a possible presence of contamination of a container with a decorative exterior, comprising:
   an irradiating means for irradiating the container with at least a first wavelength,
   a first recording means for recording a radiation sample of radiation during interaction of the radiation with at least a part of the container,
   an orientation determining means for determining a rotational orientation of the container relative to the first recording means, and
   a comparing means for comparing the sample to a reference matching the rotational orientation of the container relative to the first recording means during the recording to determine the possible presence of contamination,
   a second recording means for determining, by way of a second recording, the orientation of the container relative to the first recording means on the basis of the mutual positions and orientations of the first recording means, the second recording means and the container at the time of the first and second recording.

2. Device as claimed in claim 1, further comprising:
   a second irradiating means for emitting radiation of at least a second wavelength.

3. Device as claimed in claim 2, further comprising:
   a filter means for making recordings in optically independent manner with the first recording means on the basis of radiation of the first or of the second wavelength.

4. Device as claimed in claim 1, further comprising:
   a polarizing means for polarizing radiation of the irradiating means.

5. Device as claimed in claim 1, wherein the first radiation sources are positioned behind the container relative to the container during making of the recording wherein the radiation irradiates the container.

6. Device as claimed in claim 1, further comprising:
   a selecting means for selecting apart of the recording of a part of the container as an assessment part, on the basis of which part the assessment is carried out.

7. Device as claimed in claim 1, wherein the first recording means includes at least one camera.

8. Device as claimed in claim 3, wherein the filter means includes an optical filter.

9. Device as claimed in claim 3, wherein the filter means includes an electronic filter.

10. Device as claimed in claim 1, further comprising:
    a composing means for composing, on the basis of at least one of the radiation sample and parameters, a robust reference image or a reference image with permissible deviation values, on the basis of which image acceptable deviations in the decorative exterior within a series of containers can be taken into account during selection of containers.

11. Device as claimed in claim 1, further comprising:
    a selecting means for selecting a part of the recording of a part of the container as an assessment part, and
    a processing means for producing, on the basis of the radiation sample or the assessment part, a flat representation thereof.

12. Device as claimed in claim 11, further comprising:
    a composing means for composing, on the basis of the radiation sample, a robust reference image with permissible deviation values, wherein the comparing means are embodied in order to compare the flat representation to the robust reference image.

13. Device as claimed in claim 12, further comprising:
    a second comparing means for comparing the second recording to a second reference image or the robust reference image for the purpose of detecting deviations on the decorative exterior.

14. Device as claimed in claim 1, wherein the orientation determining means determine the orientation on the basis of the recording of the second recording means.

15. Device according to claim 1, wherein the irradiating means irradiate the container substantially from the top or bottom.

16. Method for determining a possible presence of contamination of a container with a decorative exterior, comprising:
    irradiating the container with radiation with at least a first wavelength,
    determining a rotational orientation of the container relative to a first recording device,
    recording, via the first recording device, a radiation sample of the radiation after the radiation passes through at least a part of the container,
    determining the possible presence of contamination by comparing the sample to a reference matching the rotational orientation of the container relative to the first recording device,
    approving or rejecting the container based upon the determination, and
    determining the rotational orientation of the container, making a second recording via a second recording device for determining the orientation of the container relative to the first recording device on the basis of the mutual positions and orientations of the first recording device, the second recording device and the container at the time of the recording of the sample and the second recording.

17. Method as claimed in claim 16, wherein the containers are transported via a conveyor past an irradiating device and the first recording device.

18. Method as claimed in claim 16, wherein the sample comprises an image recording and the reference comprises a reference image.

19. Method as claimed in claim 16, wherein two recording devices make the recording of the radiation sample and the second recording, respectively, at an angle relative to the container.

20. Device for determining a possible presence of contamination of a container with a decorative exterior, comprising:
   an irradiating means for irradiating the container with at least a first wavelength,
   a first recording means for recording a radiation sample of radiation during interaction of the radiation with at least a part of the container,
   an orientation determining means for determining a rotational orientation of the container relative to the first recording means, and
   a comparing means for comparing the sample to a reference matching the rotational orientation of the container relative to the first recording means during the recording to determine the possible presence of contamination,
   wherein the orientation determining means includes a second recording means for making at least a second recording for the purpose of determining the orientation of the container relative to the first recording means on the basis of the mutual position and orientation of the second recording means and the container at the time of the second recording.

21. Method for determining a possible presence of contamination of a container with a decorative exterior, comprising:
   irradiating the container with radiation with at least a first wavelength,
   determining a rotational orientation of the container relative to a recording device,
   recording, via the recording device, a radiation sample of the radiation after the radiation passes through at least a part of the container,
   determining the possible presence of contamination by comparing the sample to a reference matching the rotational orientation of the container relative to the recording device,
   approving or rejecting the container based upon the determination, and
   recording, by a second recording means, a second recording for determining the orientation of the container relative to the recording device on the basis of the mutual position and orientation of the second recording means and the container at the time of the second recording.

22. Method for determining a possible presence of contamination of a container with a decorative exterior, comprising:
   irradiating the container with radiation with at least a first wavelength,
   determining a rotational orientation of the container relative to a recording device,
   recording, via the recording device, a radiation sample of the radiation after the radiation passes through at least a part of the container,
   determining the possible presence of contamination by comparing the sample to a reference matching the rotational orientation of the container relative to the recording device,
   approving or rejecting the container based upon the determination, and
   recording, by a second recording means, a second recording for determining the orientation of the container relative to the radiation sample on the basis of the mutual position and orientation of the second recording means and the container at the time of the second recording.

23. Method for determining a possible presence of contamination of a container with a decorative exterior, comprising:
   irradiating the container with radiation with at least a first wavelength,
   determining a rotational orientation of the container relative to a recording device,
   recording, via the recording device, a radiation sample of the radiation after the radiation passes through at least a part of the container,
   determining the possible presence of contamination by comparing the sample to a reference matching the rotational orientation of the container relative to the recording device,
   approving or rejecting the container based upon the determination, and
   recording, by a second recording means, a second recording, and
   comparing, by a second comparing means, the second recording to a second reference image or a robust image for the purpose of detecting deviations on the decorative exterior.

* * * * *